United States Patent [19]

Edwards et al.

[11] 4,152,230
[45] May 1, 1979

[54] PHOTOOXIDATION PROCESS

[75] Inventors: Derek W. Edwards; Graham H. Jones, both of Runcorn, England

[73] Assignee: Imperial Chemical Industries Limited, London, England

[21] Appl. No.: 762,332

[22] Filed: Jan. 25, 1977

[30] Foreign Application Priority Data

| Feb. 6, 1976 | [GB] | United Kingdom | 4762/76 |
| Feb. 6, 1976 | [GB] | United Kingdom | 4763/76 |
| Feb. 6, 1976 | [GB] | United Kingdom | 4764/76 |
| Aug. 24, 1976 | [GB] | United Kingdom | 35183/76 |

[51] Int. Cl.$^2$ ............................................. B01J 1/10
[52] U.S. Cl. ............................ 204/158 R; 204/162 R
[58] Field of Search ......... 204/158 R, 162 R, DIG. 11

[56] References Cited

U.S. PATENT DOCUMENTS

| 3,119,875 | 1/1964 | Steinmetz et al. | 204/162 R |
| 3,591,476 | 7/1971 | Battaerd | 204/158 HE |
| 3,781,194 | 12/1973 | Juillet et al. | 204/162 R |

FOREIGN PATENT DOCUMENTS

| 624964 | 2/1936 | Fed. Rep. of Germany | 204/158 R |
| 356096 | 8/1931 | United Kingdom | 204/158 R |

OTHER PUBLICATIONS

Takeda et al., Bull. Chem. Soc. Japan, vol. 41, No. 1, p. 268, (1968).

*Primary Examiner*—Howard S. Williams
*Attorney, Agent, or Firm*—Cushman, Darby & Cushman

[57] ABSTRACT

A photochemically initiated oxidation process for organic materials using only catalytic quantities of the photochemical agent by conducting the reaction in the presence of a compound of a variable valency metal (especially copper) in order to trap the photochemically produced radicals. The spent metal compound can be regenerated ready for trapping further radicals by contact with a source of oxygen.

21 Claims, 1 Drawing Figure

GRAPH FOR EXAMPLE 13

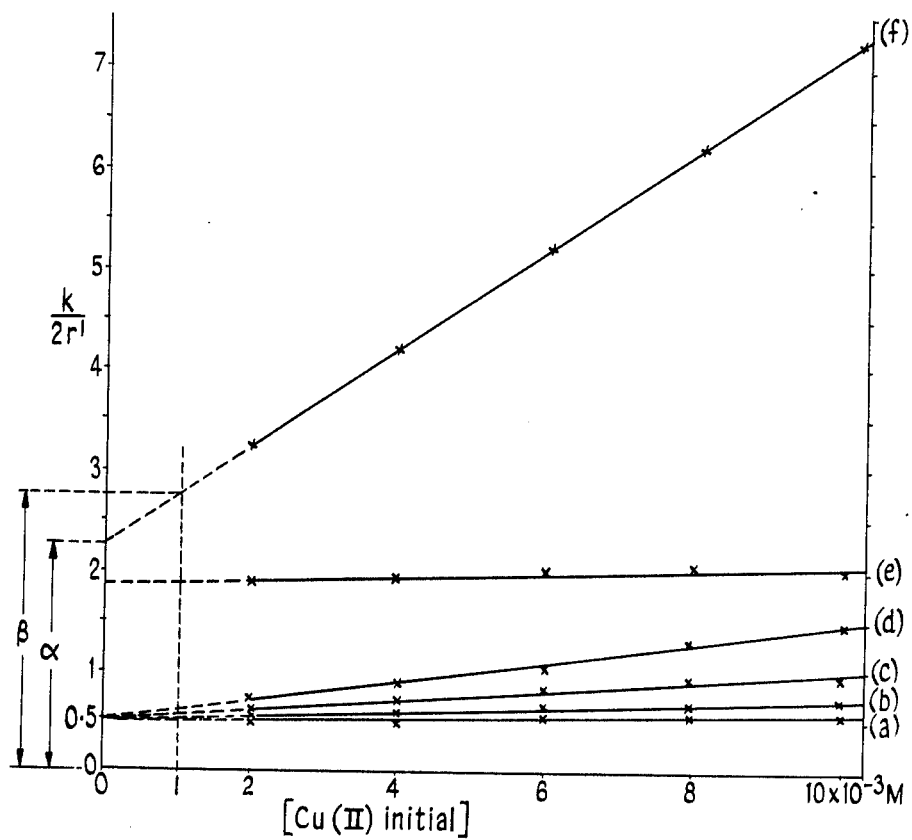
GRAPH FOR EXAMPLE 13

PHOTOOXIDATION PROCESS

The present invention relates to a process for the oxidation of organic substrates.

It is known to conduct an oxidation reaction photochemically by activating an organic oxidising agent so that it will abstract a hydrogen atom from an organic substrate. A radical species is formed by this reaction both in the organic substrate and from the activated oxidising agent which we hereinafter refer to as the hydrogen abstracting agent. A problem in many examples of this type of reaction is that these radicals tend to combine together in a variety of ways and thereby the hydrogen abstracting agent is used up and often is combined in the final product.

We have now found a way of regenerating the hydrogen abstracting agent so that the reaction is catalytic and therefore only catalytic quantities of the agent are required.

Moreover the oxidised organic substrate which is the product of the reaction may be obtained relatively free of contamination with the hydrogen abstracting agent or with the radical species therefrom.

According to the present invention there is provided a process for the oxidation of an organic substrate comprising the photo-chemical activation of an organic hydrogen abstracting agent to form a reactive species capable of abstracting a hydrogen atom from the organic substrate, one of the radicals thus produced being reconverted to the organic hydrogen abstracting agent by the presence of a compound of a variable valency metal initially present in the higher of the two valency/oxidation states and reduced to the lower of the valency/oxidation states during the process.

During the operation of the process the metal regenerates the original (i.e. the non-activated) form of the hydrogen abstracting agent and thereby it is itself reduced to the lower oxidation state. The hydrogen abstracting agent is then available for further use and may be re-activated photochemically. The metal compound may be reconverted to the higher oxidation state by contact with a conventional oxidising agent; for example if gaseous oxygen is suitable this may be conveniently carried out by admitting air to the metal compound. It will be appreciated however that although gaseous oxygen may be capable of reconverting the metal compound to the higher oxidation state, excessive amounts of oxygen are in general deleterious to the photochemical reaction. The reconversion of the metal compound would therefore normally be conducted at a time of "rest" from the main reaction i.e. either when the metal compound is physically removed from the environment of the hydrogen abstracting agent and the organic substrate or when no activation of the agent is being carried out, which means in practice for a photochemically activated agent whilst it is in the "dark." In addition the reactants or a solvent used to dissolve the reactants may be given a purge of inert gas before the photochemical reaction is commenced or recommenced in order to lower the concentration of oxygen to a level at which it does not significantly interfere with the ability of the metal compound to regenerate the original form of the abstracting agent.

When the hydrogen atom has been abstracted from the organic substrate by the photo-chemically activated species of the hydrogen abstracting agent an organic radical will be produced usually known as a "free radical". Free radicals are active organic species and those produced by the process of this invention may take part in a variety of reactions well known for organic free radicals. For example two substrate radicals may mutually combine to produce a stable oxidation product which is effectively a "dimer" of the original substrate. If the original substrate were an organic molecule a dimer would be produced comprising two molecules of the compound joined together with the loss of two hydrogen atoms—one from each molecule abstracted by the activated agent. This is the simplest aspect of the oxidation process. The organic free radicals may react in other ways for example with a radical scavenger or with a polymerisable monomer which may be deliberately introduced (preferably in carefully measured quantities) in order to achieve the products desired.

However we prefer to react or "trap" the radicals produced in the organic substrate with a metal compound which is similar to, or the same as, the metal compound which is already present in the process in order to regenerate the hydrogen abstracting agent. For this preferred aspect of the invention the metal compound would also be one in which the metal is in the higher of two valency/oxidation states. Conveniently the same metal compound will regenerate the oxidising agent and also trap the radical produced from the organic substrate and therefore no further reagents would be required to be added in order to trap the substrate free radical. The oxidation product of the process in such a case is one produced by a further oxidation of the radical in the organic substrate, in one aspect by an elimination of a further hydrogen atom to give a dehydrogenated product. For example in this aspect of the process an alkane may be oxidised to an alkene or an alkyl group in an organic compound may be converted to an alkenyl group. If the alkyl group contains more than two carbon atoms there may be alternative positions on the group for the dehydrogenated or unsaturated site. Several products are possible unless the hydrogen abstracting agent selectively operates on one site only.

However if the organic compound is a molecule with only one type of abstractable hydrogen atom one product only is possible and in this case there is no necessity to use abstracting agents which give some selectivity of position. For example cyclohexane may be oxidised to cyclohexene and by-products in this case are minimal. The process uses mild conditions in contrast to processes using high temperatures or powerful dehydrogenation agents which show a tendency to proceed further to give di or multi unsaturated products. This represents a distinctive advantage for the process of this invention over prior art oxidation or dehydrogenation processes which for example often give aromatic products from the dehydrogenation of cyclo-alkanes.

Yet a further aspect of the process of this invention is provided either by the production of compounds which arise from the formation of a carbonium ion from the free radical produced as the primary oxidation product of the organic substrate, or by the direct transfer of ligands from the metal compound to the free radical site on the organic substrate.

The metal compound used in the process is able in some environments to direct the reaction of the radical towards the formation of a carbonium ion rather than a dimeric product or an unsaturated product. If a carbonium ion is produced it is merely an intermediate usually not isolatable from the system as a true oxidation product: the product separated will be that produced by the combination of the carbonium ion and another compound present in the system, for example combination with the solvent medium.

For example the radical formed from a methyl substituted aromatic compound $Ar^1CH_3$ will be $Ar^1CH_2$. by the abstraction of a hydrogen atom from the methyl group. Instead of the direct combination of two of these radicals to form a dimer $Ar^1CH_2CH_2Ar^1$, the radical may be converted in the presence of the metal compound to the carbonium ion $Ar^1CH_2^+$. This intermediate may combine with, for example, a carboxylic acid RCOOH to give an ester which may be represented as $Ar^1CH_2OOCR$ or with, for example, an aromatic compound $Ar^2H$ by electrophilic substitution to give a compound which may be represented as $Ar^1CH_2Ar^2$. $Ar^1$ is an aromatic moiety which optionally may contain heteroatoms in the ring and/or may contain other substituents besides the $CH_3$ group, but such substituents should preferably not themselves contain readily abstractable hydrogen atoms. $Ar^2H$ may be the substrate $Ar^1CH_3$ itself or it may be an aromatic compound which is more reactive towards electrophilic substitution than is the compound $Ar^1CH_3$; when $Ar^2H$ is not the same as $Ar^1CH_3$ it should not contain competitively abstractable hydrogen atoms. RCOOH is preferably a simple aliphatic carboxylic acid without readily abstractable hydrogen atoms and which can act as solvent, for example acetic acid, or a simple aromatic carboxylic acid without readily abstractable hydrogen atoms and which is sufficiently soluble in the reaction medium, for example benzoic acid.

The aforementioned hydrogen abstracting agent is a compound possessing a functional group which, upon irradiation with light of a suitable wavelength, is converted to a higher energy state in which it is capable of abstracting hydrogen from the organic substrate. Details of potential hydrogen abstracting agents may be found in several literature sources, for example, "Mechanistic Organic Photochemistry", by D. C. Neckers, 1967, Chapter 7 (Reinhold, New York) and "Molecular Photochemistry", by N. J. Turro, 1967, Chapter 6 (Benjamin, New York).

Compounds capable of acting as abstracting agents in this context include compounds of formula $R^5COR^6$ where $R^5$ and $R^6$, which are the same or different, may be alkyl, cycloalkyl, aryl, alkaryl or aralkyl groups and $R^6$ may also be a hydrogen atom or a group $R^5CO$ or $COOR^5$. $R^5$ and $R^6$ may also contain functional substituents which do not interfere with the course of the reaction. Examples of such compounds include diaryl ketones, e.g. benzophenone or benzoylpyridine; alkyl arylcarbonyl compounds, e.g. acetophenone or acetylpyridine; aryl aldehydes, e.g. benzaldehyde; α-diketones, e.g. benzil and biacetyl; quinones, e.g. anthraquinone; and derivatives of glyoxylic acid, e.g. phenyl benzoyl formate.

Since some agents are sparingly soluble in non-polar solvents it is preferred to use substituted compounds, for example anthraquinone, substituted with one or more alkyl groups wherein the alkyl substituent is suitably a lower alkyl group for example containing up to six carbon atoms. For example 2-t-butyl anthraquinone has been found to be very much more soluble in hydrocarbon solvents and reactants e.g. cyclohexane, than anthraquinone itself.

Other hydrogen abstracting agents include acridine and nitrobenzene.

The efficiency of the aforementioned classes of compounds as hydrogen abstracting agents will, of course, vary considerably from compound to compound and with the precise nature of the organic substrate. However, a skilled photochemist will be able to assess, from literature references such as those given above, which of the potentially useful compounds will be likely to prove most suitable for his particular requirements, the final choice between several potential candidates being readily resolved by experiment.

The variable valency metal compound, used in this invention as a radical trapping agent, must be efficiently dispersed and preferably soluble to some extent in the reaction mixture and, preferably, the metal is one which is readily re-oxidised after use.

The metal compound selected for the process should possess a reduction potential (as hereinafter defined) which is not so high that the compound could oxidise the organic substrate on its own without the initial hydrogen abstraction process effected by the photochemically activated species. The advantage of the present process is that it is a catalytic process wherein both the hydrogen abstracting agent and the metal compound may be regenerated, optionally in situ, and fresh portions of the organic substrate may be oxidised without the need for a physical separation of either agent from the system for regeneration or the need for fresh agent to be added. Such would be necessary in many prior art processes wherein a similar oxidation product is produced. Accordingly we prefer to select metal compounds which possess a low but positive reduction potential, particularly for example a potential which if measured in water would be in the range from zero to 1.23 volts, since such compounds may be reoxidised by gaseous oxygen. The reduction potential is as defined in "Advanced Inorganic Chemistry", Cotton & Wilkinson, Interscience 3rd Ed. 1972, page 165. Suitable reduction potentials may be obtained from many compounds, including salts and co-ordination compounds, of the metals copper and iron and a few compounds of other metals for example the metals cobalt, manganese, chromium and vanadium may be mentioned. The metal especially preferred is the metal copper because a large range of salts, for example salts of common acids, are found to be eminently suitable for conducting the various aspects of the invention. In some aspects of the invention iron salts are also particularly useful. Also, since the variable valency metal compound is preferably completely soluble in the reaction mixture, the compound is preferably a metal salt of an organic acid as many such compounds are commonly soluble in many organic media. Metal salts used in our process are preferably salts of aliphatic and aromatic carboxylic acids, which may also contain additional neutral ligands, but metal salts of other acids for example sulphonic acids may be used if desired.

If the organic ligands on the metal compound contain abstractable hydrogens they may interfere with the selectivity of the oxidation process and cause wastage of the catalytic agents used. Therefore we prefer to use ligands derived from organic acids which either possess no hydrogen atoms or only hydrogen atoms difficult to abstract, for example aromatic hydrogen atoms or hydrogen atoms in a relatively non-activated methyl group. Preferred acids include for example benzoic, acetic, pivalic, trifluoromethyl sulphonic, benzene sulphonic, and trifluoro acetic acids, or the substrate itself if it is an acid. The strength of the acid used in the metal compound and the concentration of free acid present will affect the nature of the final oxidation product obtained.

The wavelength of the light used to irradiate the reaction mixture will, of course, depend on the exact nature of the hydrogen abstracting agent, and may be readily ascertained from the literature sources previously referred to. However, for convenience it is generally preferred to choose an abstracting agent which may be activated by irradiation with light in the near ultraviolet, for example, in the wavelength range 270 nm to 450 nm.

Without prejudice to the broader scope of the invention, it is thought that the mechanism of one aspect of our process proceeds via the following reaction scheme which, for the sake of convenience only, is illustrated by the case when the variable valency metal compound is a copper (II) carboxylate the hydrogen abstracting agent is benzophenone $\phi_2CO$ and the substrate is a compound of general formula $R^1R^2CH\text{-}CHR^3R^4$.

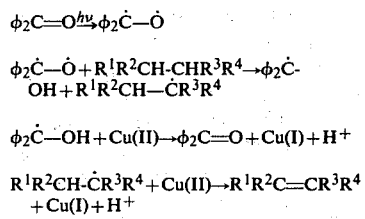

It will thus be seen that it is postulated that the abstracting agent (e.g. benzophenone) first produces a diradical which abstracts a hydrogen atom from the organic substrate producing a substrate radical and a ketyl radical. The Cu (II) then traps the ketyl radical, regenerating benzophenone and being itself reduced to Cu (I), and in addition traps the substrate radical by removing a second hydrogen atom to give an olefinically unsaturated product and again being itself reduced to Cu (I).

In these formulae, $R^1$ to $R^4$, which may be the same or different may be hydrogen atoms or alkyl, aryl, or other hydrocarbyl groups. Groups $R^1$ to $R^4$ may also comprise and/or contain functional substituents such as F, CN or COOH and may also contain functional links such as —O—, —CO— and —COO— in the hydrocarbyl groups, and two or more of $R^1$ to $R^4$ may be joined to form a ring system.

Examples of suitable substrates include acyclic, cyclic and polycyclic alkanes, and their simple derivatives, such as carboxylic acids.

However, a wide variety of organic substrates may be used, provided that they do not themselves "trap" the radicals formed or "quench" the activated hydrogen abstracting agent.

In contrast to the above reaction scheme, when the variable valency metal is omitted from the reaction mixture the abstracting agent and substrate are consumed in reactions which typically produce dimers. For example from the reaction between benzophenone and toluene the products are benzpinacol, bibenzyl and benzyl diphenyl methanol as indicated by the prior art (G. S. Hammond, JACS, 83, 2795 (1961)).

The process of our invention is performed by mixing the prescribed reactants, optionally with an inert solvent, especially if this is necessary to maintain a homogeneous liquid reaction mixture under the reaction conditions, and irradiating it with light of the appropriate wavelength. The reaction will proceed over a wide range of temperatures, although the optimum temperature for a particular reaction mixture is best established by experiment e.g. in range −50° C. to 200° C. It is convenient to conduct the reaction at the solvent or substrate reflux temperature. This serves to expel oxygen from the reaction mixture, but it is also preferred to conduct the reaction under an atmosphere of inert gas, for example, nitrogen. It may be advantageous in certain circumstances to use a gas which will react with the radicals produced, e.g. carbon monoxide.

When the variable valency metal compound is reoxidised, e.g. in the case of a copper compound by passing oxygen or air through the solution, this should only be done in the absence of irradiation, since the presence of oxygen is deleterious to the photochemical process.

Thus, in such a case, when the reaction has proceeded until almost all the copper (II) has been reduced to copper (I), as indicated by decolourisation of the blue cupric ions, the irradiating light is switched off and air or oxygen bubbled through the reaction mixture to restore the blue colour. The light is then switched on again and the process repeated. This sequence may be repeated as many times as is necessary to build up the level of product in the reaction mixture.

It will be appreciated that since the benzophenone is regenerated by reaction (c) above and the copper (I) may be re-oxidised to copper (II) by oxygen, the total reaction is catalytic on both these reagents.

The process may, of course, be carried out batchwise or continuously, provided that the regeneration of the variable valency metal compound takes place when the reaction mixture is not being irradiated.

This may be accomplished, for example, by continuously removing a portion of the reaction mixture from the irradiation zone and transferring it to a regeneration zone where it comes into contact with oxygen. After regeneration it is returned to the irradiation zone, after removal of excess oxygen.

According to a particular form of the present invention, a process for the selective oxidation of a compound formula

to a compound formula

comprises contacting the compound of formula (1) with a hydrogen abstracting agent (as hereinbefore defined) and irradiating the abstracting agent with light of a wavelength capable of exciting the agent to a state in which it will abstract a hydrogen atom from the compound of formula (1), the reaction being conducted in the presence of a compound of a variable valency metal initially in the higher of two valency/oxidation states which is capable of oxidising both of the radicals produced by the hydrogen abstraction and which thereby regenerates the hydrogen abstracting agent and converts the compound of formula (1) to an intermediate which will form a compound of formula (2) by means of a reaction with an acid of formula $R^4COOH$, a process wherein Ar is an aromatic nucleus;

$R^1$ $R^2$ and $R^3$, which may be the same or different, represent hydrogen atoms, aromatic or saturated or unsaturated aliphatic hydrocarbyl groups;

Y is either a direct link or is an —O—, —CO—,

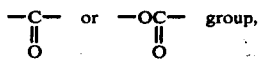

provided that such groups $R^1Y$, $R^2$, $R^3$ do not contain readily abstractable hydrogens, and any of $R^1$, $R^2$ and $R^3$ may be linked alone or in conjunction with the aromatic nucleus to form a further ring system; n is a small integer and $R^4$ is an aliphatic or aromatic hydrocarbyl group optionally containing substituents but which does not contain readily abstractable hydrogen atoms.

The product may be separated from the reaction mixture by any convenient means including fractional distillation, fractional crystallisation, or chromatography. Alternatively the product may be converted by a subsequent process to another compound which is more easily separable.

The process of our invention enables certain reactions to be carried out cleanly and conveniently in a single stage under relatively mild conditions to produce compounds which would otherwise be difficult to produce or at least require a multi-stage process. It may be desirable to continuously remove the product as it is formed because it is more reactive than the substrate. For example in the reaction of benzophenone and copper pivalate with cyclohexane the major by-product, cyclohexenyl pivalate, can be minimised by removing the cyclohexene as it is formed.

As especially useful reaction at the production of 3 phenoxy benzyl acetate from 3 phenoxy toluene (3 methyl diphenyl oxide) by photochemical reaction with benzophenone in the presence of copper (II) acetate and glacial acetic acid. Additionally we have found that primary and secondary alcohols may be oxidised catalytically to aldehydes and ketones respectively by the process of this invention for example benzyl alcohol to benzaldehyde or isopropyl alcohol to acetone.

According to a preferred embodiment of the present invention there is provided an oxidation process conducted by means of the photochemical activation of a benzophenone or anthraquinone compound to form reactive species capable of abstracting a hydrogen atom from an organic substrate, the radicals thus produced being reconverted to the benzophenone or anthraquinone compound by the presence of a compound of copper initially in the higher valency state, namely copper (II).

A medium-pressure mercury lamp is a convenient source of light because many benzophenones exhibit absorption of wavelengths extending up to ca. 380 nm while many athraquinones exhibit absorption of wavelengths up to 440 nm.

The nature of the products of the reaction may depend not only upon the reactants used but also upon the conditions of the reaction for example the ligands attached to the copper (II) ions in the copper compound and the solvent/diluent medium in which the compound is dissolved. For example cyclohexane may be converted to cyclohexene using copper acetate monohydrate and pivalic acid but if the same copper salt is used with a stronger acid for example p-toluene sulphonic acid hydrate or trifluoromethane sulphonic acid dissolved in acetic acid the major oxidation product observed is cyclohexyl acetate.

The benzophenone or anthraquinone compounds used may be the unsubstituted parent compound benzophenone or anthraquinone. However it is preferred to conduct the reaction under homogeneous conditions and therefore the reactants should be easily soluble or miscible together. Accordingly since anthraquinone is sparingly soluble in non-polar solvents it is preferred to use substituted anthraquinones for example substituted with one or more alkyl groups wherein the alkyl substituent is suitably a lower alkyl group for example containing up to six carbon atoms. For example 2-t-butyl anthraquinone has been found to be very much more soluble in hydrocarbon solvents and reactants e.g. cyclohexane, than anthraquinone itself.

The nature of the abstracting agent may modify the course of the reaction and particular abstracting agents may be chosen accordingly. For example a variant which may be employed is to use a photochemically-active species deposited on an inert support. This may be seen to have advantages in the ease of removal of the abstracting agent from the reaction mixture for example in a case where the product is required in a specially pure condition or where the abstracting agent would be difficult to separate.

Special substituents on the abstracting agent may affect the course of the reaction by reason of some regio-selectivity imparted by the substituent. The activated species could for example, because of the substituent, abstract a particular hydrogen atom from the substrate in preference to others. This may take place because of interactions between the abstracting agent (or the substituents thereof) and the substrate which then promotes attack by the abstracting agent at favoured positions on the substrate. These interactions may include hydrophobic, electrostatic, hydrogen-bond, charge-transfer or other physico-chemical forces.

The interactions between a photochemically activated species and a substrate which may be used to advantage in the present invention may be those for example which have been used in the case of carboxylic acid derivatives of benzophenone and substrates containing a carboxylic acid group whereby selectively coupled products were obtained (R. Breslow and P. C. Scholl JACS 93, 2332, (1971).

Likewise if a benzophenone derivative or an anthraquinone derivative is laid down on a support which interacts with a reactive substrate in a selective manner, the reaction may be caused to progress in a different way which would not be possible without the selectivity imparted by the support and its interaction with the substrate.

One method is to absorb the substrate onto or into an added material, which might be heterogeneous (e.g. silica) or homogeneous (e.g. a cyclodextrin) with the substrate, in such a way that only certain positions on the substrate when absorbed remain accessible for attack by the abstracting agent. In addition the abstracting agent may be chemically bonded to this added material thus enhancing the "binding site" selectivity herein described.

If interactions between the abstracting agent and the substrate result in some geometrically preferred structure within the complex, then it could be expected that hydrogen abstraction from the substrate would take place from certain particularly accessible positions within this complex. Instead of or in addition to this the direction of elimination to form an olefin from the copper-substrate radical complex could be controlled by the nature of the ligands attached to the copper (II), (for example, if for instance they are bulky or asymmetric) so as to form a particular olefin preferentially.

In order to cause the abstracting agent (for example benzophenone) to complex with the substrate in an ordered manner various well known types of dynamic interactions may be used. Such interactions include "hydrophobic bonding" (such as occurs between cyclodextrins and many hydrocarbons, and between bile acids and various hydrocarbons, in aqueous solution), hydrogen bonding (such as occurs between crown ethers and various primary alkyl ammonium salts and between pairs of carboxylic acids, in solvents such as benzene and acetonitrile), transient ester formation (such as occurs between boric acid and alcohols in solvents such as benzene and acetonitrile), and electrostatic bonding (such as is present in tetraalkylammonium carboxylates) and in metal ion coordination (for example in mixed carboxylic acids salts of copper (II)). In order to make use of such interactions the abstracting agent (for example benzophenone) would be attached to a "binding site" (e.g. a cyclodextrin, a crown ether, a carboxylic acid, a borate, a tetra alkylammonium ion, or a metal ion) in such a way that when the substrate is complexed with this binding site it suffers regioselective hydrogen abstraction by the abstracting agent.

Also, since certain compounds form micelles or aggregates in solution which can trap added foreign molecules it is possible to produce structured complexes of an abstracting agent in the presence of aggregates of substrate, or vice-versa. For instance sodium deoxycholate is known to dissolve various hydrocarbons in water by micellar-inclusion. Such a complex in which the abstracting agent was the included molecule should enable the deoxycholic acid to be regioselectively attacked. In this case the "binding sites" would simply be the hydrophobic interactions between the abstracting agent and the substrate themselves.

The invention is illustrated by the following Examples, in which all parts are by weight.

EXAMPLE 1

A mixture of benzophenone (2 parts), copper acetate monohydrate (1 part) and toluene (80 parts) was dissolved in glacial acetic acid (500 parts) in a round-bottom flask, equipped with a condenser, gas inlet and magnetic stirrer. Air was displaced from the flask by a stream of nitrogen and the blue solution heated to its reflux temperature, while maintaining the stream of nitrogen. The solution was then irradiated by means of an external ultra-violet lamp. As the reaction proceeded the blue colour was gradually discharged and the lamp was switched off before the solution was completely decolourised. Air was then admitted to the flask and the solution stirred until the blue colour was restored, indicating re-oxidation of the copper. This procedure was repeated 10 times after which the solution was distilled under reduced pressure to remove most of the toluene and acetic acid. The residue was then dissolved in toluene and extracted with dilute (1% vol/vol) sulphuric acid, then dilute (1% vol/vol) sodium hydroxide and, finally, water. The organic layer was then dried and excess toluene removed by distillation. When the residue was analysed by nuclear magnetic resonance (nmr) spectroscopy, the spectrum indicated the presence of benzyl acetate, benzophenone and a small amount of dibenzyl.

EXAMPLE 2

The procedure of Example 1 was repeated but a small amount of a strong acid, toluene sulphonic acid (2 parts), was added to the solution. The nmr spectrum of the products this time indicated the presence of benzyl acetate and benzophenone, but only a trace of dibenzyl.

EXAMPLE 3

The procedure of Example 2 was repeated using 5 parts of benzophenone, 1 part of copper acetate monohydrate and 50 parts of 3-phenoxytoluene in 250 parts of glacial acetic acid. When the product-containing residue was analysed by nmr, the spectrum indicated the presence of 3-phenoxybenzyl acetate, benzophenone and 3-phenoxy toluene. A pure sample of 3-phenoxy benzyl acetate was isolated from this residue by column chromatography on silica gel. This sample was characterised by nmr, mass spectrometric and infra red comparisons with a sample of authentic material.

EXAMPLE 4

A mixture of benzophenone (1 part), copper acetate monohydrate (1.5 parts), benzoic acid (10 parts), and n-hexadecane (80 parts) was dissolved in benzene (800 parts) in a round-bottom flask, equipped with a condenser, gas inlet and magnetic stirrer. Air was displaced from the flask by a stream of nitrogen and the blue solution heated to its reflux temperature, while maintaining the stream of nitrogen. The solution was then irradiated by means of an external ultra-violet lamp. As the reaction proceeded the blue colour was gradually discharged and the lamp was switched off before the solution was completely decolourised. Air was then admitted to the flask and the solution stirred until the blue colour was restored, indicating re-oxidation of the copper. The whole procedure was repeated six times, after which the mixture was extracted with dilute (1% vol/vol) sulphuric acid, then dilute (1% wt/vol) sodium hydroxide and, finally, water. The organic layer was then dried and excess benzene removed by distillation. When the residue was analysed by nuclear magnetic resonance (nmr) spectroscopy, the spectrum indicated the presence of olefinic protons at $4.6\tau$, consistent with an internal double bond, and at $4.2\tau$ and $5.1\tau$, consistent with a terminal double bond. The ratio of benzophenone to olefinic products was, by integration, approximately 1 to 3.

EXAMPLE 5

A mixture of 4-benzoylbenzoic acid (1 part), copper stearate (1.5 parts) and stearic acid (6.5 parts) was dissolved in benzene (180 parts), and reacted and Cu (II) regenerated as in Example 4. The procedure was repeated five times, stopping each irradiation period before the blue colour was completely discharged. The mixture was then extracted with dilute (1% vol/vol) sulphuric acid, and then with water. The organic layer was dried and excess benzene removed by distillation.

A portion of the residue was examined by nmr spectroscopy, which showed the presence of olefinic protons at $4.6\tau$. Integration suggested that approximately 8% of the stearic acid had been converted to unsaturated acids.

A second portion of the residue was treated with $BF_3$ in methanol. Examination of the methyl esters of this carboxylic acid mixture by gas liquid chromatography (glc) showed, besides methyl stearate, a compound (or mixture of compounds) with the same retention characteristics as methyl oleate.

EXAMPLE 6

A mixture of benzophenone (2 parts), copper acetate monohydrate (1 part), benzoic acid (6 parts), and tetralin (40 parts) was dissolved in benzene (400 parts), and reacted and Cu (II) regenerated as in Example 4. The procedure was repeated five times, after which the mixture was extracted with dilute (1% vol/vol) sulphuric acid, then dilute (1% wt/vol) sodium hydroxide and, finally, water. The organic layer was dried and excess benzene removed by distillation. When the residue was analysed by nmr spectroscopy, the spectrum indicated the presence of olefinic protons at 3.7$\tau$ and 4.2$\tau$ with coupling constants consistent with that expected for 1,2 dihydronaphthalene.

EXAMPLE 7

A mixture of benzophenone (2 parts), copper acetate monohydrate (1 part) and benzoic acid (3 parts) was dissolved in sufficient toluene to form a homogeneous solution (ca. 1000 parts) in a round-bottom flask, equipped with a condenser, gas inlet and magnetic stirrer. Air was displaced from the flask by a stream of nitrogen and the blue solution heated to its reflux temperature, while maintaining the stream of nitrogen. The solution was then irradiated by means of an external ultra-violet lamp. As the reaction proceeded the blue colour was gradually discharged and the lamp was switched off before the solution was completely decolourised. Air was then admitted to the flask and the solution stirred until the blue colour was restored, indicating re-oxidation of the copper. The whole procedure was repeated eight times, after which the mixture was extracted with dilute (1% vol/vol) sulphuric acid, then dilute (1% wt/vol) sodium hydroxide and, finally, water. The organic layer was dried and excess toluene removed by distillation. When the residue was analysed by nmr spectroscopy the spectrum indicated that the major product was dibenzyl together with recovered benzophenone. By integration, the amount of dibenzyl was consistent with the total amount of copper (II) which had been reduced.

EXAMPLE 8

A mixture of benzophenone (4 parts), iron (III) acetylacetonate (1 part) and toluene (130 parts) was dissolved in glacial acetic acid (500 parts) in a round-bottom flask, equipped with a condenser, gas inlet and magnetic stirrer. Air was displaced from the flask by a stream of nitrogen and the orange-brown solution heated to its reflux temperature while maintaining the stream of nitrogen. The solution was then irradiated by means of an external ultra-violet lamp. As the reaction proceeded the orange-brown colour was gradually discharged and the lamp was switched off before the solution was completely decolourised. Air was then admitted to the flask and the solution stirred until the orange-brown colour was restored, indicating re-oxidation of the iron. The whole procedure was repeated five times after which the mixture was distilled under reduced pressure to remove most of the toluene and acetic acid. The residue was then dissolved in toluene and extracted with dilute (1% vol/vol) sulphuric acid, then dilute (1% wt/vol) sodium hydroxide and, finally, water. The organic layer was dried and excess toluene removed by distillation. When the residue was analysed by nmr spectroscopy the spectrum indicated that the major product was dibenzyl together with recovered benzophenone.

EXAMPLE 9

A mixture of benzophenone (2 parts), copper acetate monohydrate (1 part) and trifluoroacetic acid (5 parts) was dissolved in toluene (500 parts) in a round-bottom flask, equipped with a condenser, gas inlet and magnetic stirrer. Air was displaced from the flask by a stream of nitrogen and the green solution heated to its reflux temperature while maintaining the stream of nitrogen. The solution was then irradiated by means of an external ultra-violet lamp. As the reaction proceeded the green colour was gradually discharged and the lamp switched off before the solution was completely decolourised. Air was then admitted to the flask and the solution stirred until the green colour was restored, indicating re-oxidation of the copper. The whole procedure was repeated three times after which the mixture was extracted with dilute (1% vol/vol) sulphuric acid, then dilute (1% wt/vol) sodium hydroxide and, finally, water. The organic layer was dried and excess toluene removed by distillation. When the residue was analysed by nmr spectroscopy the spectrum indicated that the major products were a mixture of benzyl toluenes together with recovered benzophenone and a little benzyl trifluoroacetate.

EXAMPLE 10

A mixture of benzophenone ($3 \times 10^{-2}$M), copper (II) acetate monohydrate ($5 \times 10^{-3}$M) and p-toluene sulphonic acid hydrate ($1.5 \times 10^{-2}$M) was dissolved in a 1:1 (v/v) mixture of cyclohexane and acetic acid and irradiated under nitrogen at reflux. The lamp was switched off when the initially almost-colourless solution began to turn brown and cloudy, and air was passed into the solution for a few minutes until the solution was again almost colourless. The above procedure was repeated eight times, after which the mixture was diluted with cyclohexane and extracted three times with water. The dried cyclohexane layer was distilled to remove excess cyclohexane and the residue examined by nmr spectroscopy. The major identified product was cyclohexyl acetate, which was confirmed by glc comparison with an authentic sample.

When the above experiment was repeated but with the p-toluene sulphonic acid hydrate replaced by trifluoromethane sulphonic acid, the major identified product was again cyclohexyl acetate.

EXAMPLE 11

A mixture of benzaldehyde ($2.7 \times 10^{-3}$M), copper (II) acetate monohydrate ($5 \times 10^{-3}$M) and benzoic acid ($4 \times 10^{-2}$M) was dissolved in benzyl alcohol and irradiated in an apparatus in which the solution could be quantitatively monitored for copper (II) concentration by colorimetry. When the absorbance due to copper (II) had fallen to about 20% of its original value the lamp was switched off and the solution treated with air until the absorbance reading had returned to its former value. This process of irradiation followed by treatment with air was repeated four times. On each occasion it was noted that the rate of the reaction was increasing in a manner consistent with the conversion of benzyl alcohol to benzaldehyde.

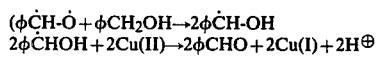

EXAMPLE 12

A mixture of 2-t-butylanthraquinone ($1 \times 10^{-2}$M), copper (II) acetate monohydrate ($1 \times 10^{-2}$M) and pivalic acid ($1 \times 10^{-1}$M) was dissolved in cyclohexane and irradiated at room temperature under nitrogen in the apparatus described in Example 11. When 75% of the copper (II) had been reduced the lamp was switched off and air bubbled through the solution until all the copper (I) was reoxidised back to copper (II). A little cyclohexane was added to make the solution back up to its original volume and after bubbling nitrogen through the solution for a few minutes the solution was reirradiated and the above precedure repeated. After ten recycles of the solution through the same sequence the mixture was analysed by glc. The yield of cyclohexene based on the total amount of copper (II) reduced was found to be $82 \pm 10\%$ of that expected.

When this reaction was repeated, and more care was taken to minimise solvent losses, the yield of cyclohexene based on the total amount of copper (II) reduced was found to be $98 \pm 7\%$.

When this reaction was repeated, but benzophenone ($3 \times 10^{-2}$M) was used in place of the 2-t-butylanthraquinone, the yield of cyclohexane based on the total amount of copper (II) reduced was found to be $96 \pm 4\%$.

EXAMPLE 13

When benzophenone is irradiated in cyclohexane the rate at which it produces cyclohexyl radicals is related to the quantum efficiency of the reaction. In the absence of copper (II), this rate is also the rate of disappearance of benzophenone resulting from its reduction. If $\phi$ max is the maximum quantum efficiency of the reaction and $\Gamma$ max is the observed rate of abstraction from cyclohexane then $\phi$ max $\alpha$ $\Gamma$ max. Normally $\Gamma$ max is measured by observing the rate of disappearance of benzophenone.

When benzophenone is irradiated in cyclohexane in the presence of copper (II), the rate $\Gamma'$ at which it produces cyclohexyl radicals is related to the quantum efficiency of this reaction $\phi\Gamma'$. This quantum efficiency will be less than $\phi$ max because of the presence of copper (II) and copper (I). Both copper (II) and copper (I) competitively absorb some of the light which would otherwise be used to activate the benzophenone, and both cause triplet benzophenone radicals to undergo quenching. We have chosen to measure the new rate $\Gamma'$, and hence new quantum efficiency $\phi\Gamma'$, by observing the rate of disappearance of copper (II), since by our mechanism they are related by a factor of two.

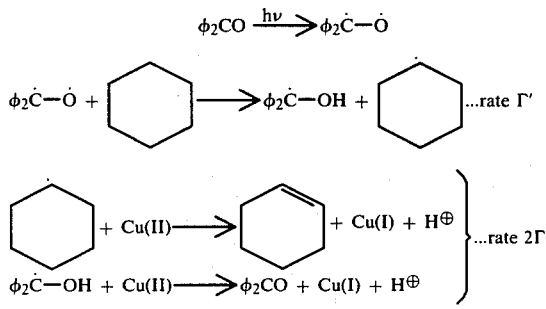

At very low concentrations of copper, $\Gamma'$ approaches the value of $\Gamma$ max and hence the value of $\phi\Gamma'$ approaches $\phi$ max.

An apparatus was designed to allow the process of the irradiations to be followed by colorimetry. An irradiation vessel was fitted with a gas inlet, a water condenser and gas outlet, an internal water cooling coil and an inlet and outlet via which a sample of the reaction mixture could be continuously analysed. This outlet was connected by tubing to a flow-cell mounted in a colorimeter, set to observe colour changes in the 600 to 700 nm region, and via a pump the tubing led back to the irradiation vessel inlet. During irradiation the reaction mixture was maintained under an atmosphere of nitrogen.

From a stock solution of cyclohexane containing copper (II) acetate monohydrate ($1 \times 10^{-2}$M) and pivalic acid ($1 \times 10^{-1}$M) solutions of different copper (II) concentrations were prepared by dilution with cyclohexane. To each of these solutions was added benzophenone ($3 \times 10^{-2}$M).

Each of these solutions was stirred under nitrogen and irradiated in the vessel at approximately 30° C. The change in copper (II) concentration with time was recorded by a pen-recorder connected to the colorimeter. The rate of disappearance of copper (II) was recorded for each of the solutions at the point where half the initial concentration of copper (II) had been consumed, and the reciprocals of these rates calculated. A graph of these reciprocal rates $1/2\Gamma'$ multiplied by an arbitrary constant chosen to give a convenient scale was plotted against initial copper (II) concentrations and a straight line with an intercept produced which gave a measure of the maximum rate of reaction ($\Gamma$ max) at essentially zero initial copper (II) concentration.

The above procedure was repeated using the same concentrations of copper (II) in cyclohexane but replacing the benzophenone by 2-t-butyl anthraquinone ($3 \times 10^{-2}$M).

In addition the procedure was repeated for the solvents isopropanol and toluene, using benzophenone or 2-t-butylanthraquinone.

The results obtained for different solutions are shown in the graph.

The graph demonstrates that this reaction is consistent for different abstracting agents in a variety of substrate solvents of differing reactivity.

To obtain relative rates from this graph, the value of $k/2\Gamma'$ at for example [Cu(II)initial]$=1 \times 10^{-3}$M is divided into the $k/2\Gamma'$ value at zero [Cu(II)]. For example, for line (f), the relative rates are $\alpha/\beta = 0.82$ and corresponding value for line (a)$=0.98$. These two figures are the two extremes for the 6 lines plotted. Thus quantum efficiencies of better than 80% of those obtainable in the absence of copper ions can be obtained for solutions containing initial concentrations of copper (II) below $1 \times 10^{-3}$M.

The relative values of $\phi\Gamma'$, for 2-t-butylanthraquinone and $\phi\Gamma'$ for benzophenone may change significantly with a different lamp which has different characteristics. The lamp used gave unfiltered, non-monochromatic light, but most of the light which activates the ketones and quinones is due to the 365 nm band.

The results reveal that in neat cyclohexane (and other similar hydrocarbon substrates) very little of the available light is wasted as a result of the presence of low concentrations (e.g. $< 1 \times 10^{-3}$M) of the copper (II) and copper (I) species in the solution.

EXAMPLE 14

Using the apparatus described in Example 13, the effect of different olefins on the rate of reaction of benzophenone with cyclohexane was studied. To a solution of benzophenone ($3 \times 10^{-2}$M), copper (II) acetate monohydrate ($5 \times 10^{-3}$M) and pivalic acid ($5 \times 10^{-2}$M) in cyclohexane was added on olefinic compound ($2 \times 10^{-1}$M). the solution was stirred at room temperature under nitrogen and irradiated until almost decolorised. The time taken for a particular change in absorbance readings, measured by the colorimeter, was noted and compared with the time taken in the absence of olefin. The procedure was repeated with fresh solutions for a series of olefins and the results are shown in the table. All results are quoted as being relative to an arbitrary time of 1 unit for the rate of decolorisation of copper (II) in the absence of added olefin.

| Olefin added ($2 \times 10^{-1}$M) | Time to reduce unit quantity of Cu(II) |
|---|---|
| none | 1 |
| 1-heptene | 1 |
| 1-decene | 1 |
| 1-hexadecene | 1.03 |
| trans-4-octene | 1.05 |
| elaidic acid | 1.2 |
| cis-4-octene | 1.6 |
| oleic acid | 1.6 |
| cyclohexene | 1.5 |
| cyclooctene | 2 |
| cis,cis-1,5-cyclooctadiene | 3.8 |
| cholesterol acetate | 1.25 |
| vinyl acetate | 1.1 |
| 1,1-dichloroethylene | (decomposes) |
| 1,4-pentadiene | 83 |
| α-methylstyrene | 77 |
| methyl methacrylate | 3.7 |

Those olefins which have least effect on the rate have values in the table of close to unity. Those olefins which react rapidly with the benzophenone radicals produced have values much greater than unity, because the rate of hydrogen abstraction (and hence copper (II) decolorisation) is markedly reduced.

The results suggest that certain de-hydrogenation processes could not be carried out satisfactorily by the invention because even small quantities of olefinic product would produce strong product-inhibition of the reaction rate by triplet quenching:ethyl benzene to styrene would be an example of this.

However in other cases the rate of slowing down of the reaction as the olefinic product builds up is much less marked, e.g. the dehydrogenation of simple straight chain paraffins. Each in these cases however it would be desirable to remove the olefin continually so that its concentration would not rise too high and prevent a reasonable rate of reaction being maintained or promote secondary attack by the abstracting agent.

EXAMPLE 15

Using the apparatus described in Example 13, the catalytic nature of benzophenone in the presence of copper (II) was examined. A solution of benzophenone ($3.5 \times 10^{-4}$M), copper (II) acetate monohydrate ($5 \times 10^{-3}$M) and pivalic acid ($5 \times 10^{-2}$M) in cyclohexane was irradiated under nitrogen at room temperature until the absorbance reading on the colorimeter indicated that 20% of the copper (II) was left. The time taken for the absorbance reading to change from 90% to 20% of its original value was recorded. A second solution of benzophenone ($5 \times 10^{-4}$M), copper (II) acetate monohydrate ($5 \times 10^{-3}$M) and pivalic acid ($5 \times 10^{-2}$M) was also irradiated under nitrogen at room temperature until the absorbance reading on the colorimeter indicated that 20% of the copper (II) was left. The lamp was switched off and this solution reoxidised by passing air into the solution until the absorbance reading on the colorimeter indicated reoxidation of the copper (I) to copper (II). This process of irradiation followed by air treatment was repeated on this second solution eight times after which the rate of consumption of copper (II), measured as the time taken for the absorbance reading to change from 90% to 20% of its original value, was the same as that rate measured for the first solution which had contained 30% less benzophenone. By assuming that the second solution now contained only $3.5 \times 10^{-4}$M benzophenone, and knowing the total amount of copper (II) which had been reduced, an estimate of the average turnover number for the catalytic activity of the benzophenone was obtained and found to be a little greater than 100.

Similarly the solvent isopropanol was examined and it was found that benzophenone was able to convert an average of a little more than 100 mole equivalents of isopropanol to acetone.

Likewise 2-t-butylanthraquinone was examined in place of benzophenone and in the solvents cyclohexane, toluene, and isopropanol. In each case the results suggested that this ketone was able to convert an average of more than 100 mole equivalents of these solvents into products before being irreversibly consumed.

EXAMPLE 16

Using the apparatus described in Example 13, the likely importance of decomposition of the copper (II) catalyst was estimated as a percentage of the overall reaction, for the particular case of copper (II) pivalate. A mixture of benzophenone ($3 \times 10^{-2}$M), copper (II) acetate monohydrate ($5 \times 10^{-3}$M) and pivalic acid ($5 \times 10^{-2}$M) was dissolved in cyclohexane and irradiated at room temperature under nitrogen. The time taken for the concentration of the copper (II) to be reduced to half was noted. This experiment was repeated first of all in toluene and then using solvents from which hydrogen is not easily abstracted, namely acetic acid and benzene in place of cyclohexane. In addition the above experiment was repeated in cyclohexane and benzene but the benzophenone was omitted. The relative times for the half-disappearance of copper (II) in each of the solutions are compared in the table below, using an arbitrary value of 1 unit of time for the reaction in cyclohexane in the presence of benzophenone.

When copper (II) is decolorised in a cyclohexane solution containing benzophenone, it could be argued that much of this decolorisation is due not to trapping of cyclohexyl radicals, but simply to photodecomposition of the copper (II) carboxylate.

However since the rate in solvents from which hydrogen is not easily abstracted was over 100 times slower than the rate of decolorisation in cyclohexane, the importance of photodecomposition of the copper salt in the cyclohexane experiment is likely to be <1% of the main reaction.

The results were as follows:

| solvent | benzophenone added | relative time for half-consumption of copper (II) |
|---|---|---|
| cyclohexane | yes | 1 |
| toluene | yes | 4.5 |
| benzene | yes | 160 |
| acetic acid | yes | 140 |
| cyclohexane | no | too slow to measure |
| benzene | no | too slow to measure |

EXAMPLE 17

It is known that pinacols may be thermally cleaved to produce radicals of the type $R^1R^2C$—OH.

At reflux in a sufficiently high boiling solvent e.g. toluene, each pinacol is in equilibrium with its radical:

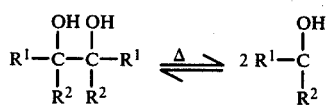

A mixture of benzpinacol ($1.25 \times 10^{-2}$M), copper (II) acetate monohydrate ($1.5 \times 10^{-3}$M) and pivalic acid ($1.5 \times 10^{-2}$M) was dissolved in toluene at room temperature. Nitrogen was passed into the solution, and the mixture heated to reflux. After about 2 minutes the initially blue solution was colourless.

The above experiment was repeated but benzpinacol was replaced by 2,3-diphenyl butane-2,3-diol ($1.25 \times 10^{-2}$M). After heating the mixture for about 40 minutes at reflux the solution was colourless.

The above experiment was repeated but the pinacol used was 2,3-dimethylbutane-2,3-diol ($1.25 \times 10^{-2}$M). After heating the mixture for about 3½ hours at reflux the solution was colourless.

These experiments conducted under non-photochemical conditions are consistent with the mechanism.

$$\phi_2\dot{C}\text{—OH} + Cu(II) \rightarrow \phi_2CO + Cu(I) + H^+$$

and also support the mechanism proposed for the overall photochemical oxidation.

Because the relative radical stabilities are $$\phi_2\dot{C}\text{—OH} > \phi Me\dot{C}OH > Me_2\dot{C}OH$$

benzpinacol produces radicals much more easily than the others upon heating. Hence because the copper (II) traps the radicals as soon as they are formed, the benzpinacol-containing solution is decolorised fastest.

EXAMPLE 18

A solution of benzophenone ($2 \times 10^{-2}$M) in toluene was irradiated under nitrogen at reflux until analysis by UV spectrophotometry at 350 nm indicated that very little benzophenone remained. The mixture was split into two portions. The first was distilled at reduced pressure to remove excess solvent and examined by proton nmr spectrometry in CDCl$_3$. Integration of the peaks at 6.4τ ($\phi\underline{CH_2}$—C(OH)$\phi_2$), 6.9τ ($\phi_2$C($\underline{OH}$)—C-($\underline{OH}$)$\phi_2$), 7.1τ ($\phi\underline{CH_2CH_2}\phi$) and 7.7τ ($\phi CH_2$—C-($\underline{OH}$)$\phi_2$), suggested that the products, benzpinacol, bibenzyl, and benzyldiphenylmethanol were present in an approximate ratio of 1:1 to 1.7 resp. Peaks at 6.9 and 7.7τ disappeared upon treatment with D$_2$O.

To the second portion of the mixture was added copper (II) acetate monohydrate ($5 \times 10^{-3}$M) and benzoic acid ($4 \times 10^{-2}$M) and the mixture heated at reflux under nitrogen. The solution decolorised within a few minutes. The mixture was cooled and air passed into the solution until the blue colour was restored. The solution was then re-heated at reflux under nitrogen. This process was repeated until the blue colour was no longer discharged from the solution. This mixture was split into two portions. The first was extracted with dilute (1% w/v) sulphuric acid, then with dilute (1% w/v) sodium hydroxide, and finally with water. The organic layer was dried, evaporated under reduced pressure, and the residue examined by nmr spectrometry. There was no peak at 6.9τ but a doublet at 2.2τ was clearly visible (assignable to the orthoprotons of benzophenone) which had not been present in the spectrum prior to treatment of the solution with copper (II). The peaks at 6.4, 7.1 and 7.7τ were still present with unchanged relative integrals.

To the second portion of this second mixture was added more benzophenone ($2 \times 10^{-2}$M) and the solution irradiated at reflux under nitrogen until pale blue. The lamp was switched off, the solution cooled, and air passed into it until the deep blue colour was restored. This process of irradiation under nitrogen followed by treatment with air was repeated five times. The mixture was cooled, extracted, and evaporated as above, and examined by nmr spectrometry. The peak at 7.1τ had increased in size relative to the previous spectrum, but the peaks at 6.4 and 7.7τ were judged to be unchanged suggesting that the benzyl diphenyl methanol had survived the irradiation conditions.

A mixture of benzophenone ($2 \times 10^{-2}$M), copper (II) acetate monohydrate ($3.75 \times 10^{-3}$M) and benzoic acid ($2.5 \times 10^{-2}$M) was dissolved in toluene and irradiated under nitrogen at reflux until the solution was pale blue. The lamp was switched off, the solution cooled, and air passed into it until the deep blue colour was restored. This process of irradiation under nitrogen followed by treatment with air was repeated nine times taking care each time not to allow the solution to completely decolorise during irradiation. The mixture was cooled, extracted and evaporated as above and examined by nmr spectrometry. Even at high sensitivity no trace of a peak at 6.4τ could be detected. A synthetic mixture of bibenzyl (100 mg) and authentic benzyl diphenyl methanol (1.5 mg) in CDCl$_3$ was examined by nmr spectrometry, and by reference to this spectrum (in which the peak at 6.4τ was clearly visible) it was calculated that the products of the irradiation experiment must have contained less than 1% of benzyl diphenyl methanol relative to dibenzyl.

(This experiment suggests that the importance of cage-dimerisation of the radical pair is small

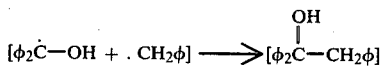

and confirms the results of Example 15.)

EXAMPLE 19

A variety of abstracting agents were examined in solvents in which they were soluble. In most cases the solvents were cyclohexane or toluene, though occasionally methanol, isopropanol, or an alcohol-water mixture was used.

The time to decolorise a solution containing a standard concentration of copper (II) was compared with the time using benzophenone. Of all the compounds tested the benzophenone and anthraquinone classes were in general the most active, and are the preferred ones. Particularly preferred are members of these classes which are soluble in the reaction mixtures: for example 2-t-butylanthraquinone is much more soluble that anthraquinone in cyclohexane.

As a result of these observations the abstracting agents could be classified and grouped according to their chemical structure and activity as follows:

(1) rate not less than 30% of that observed for benzophenone (2) rate 5 to 30% of the rate observed for benzophenone (3) rate <5% of the rate observed for benzophenone

* decomposition and/or other side reactions noted 1 crude sample of lumiflavin used, but decolorisation was observed.

A. Simple aliphatic ketones: acetone (2), butanone (2), methyl-t-butyl ketone (2).

B. Aliphatic diketones: biacetyl (3), camphorquinone (2), acetylacetone (3).

C. Aromatic ketones: acetophenone (1), trifluoroacetophenone (1), 3-acetyl pyridine (1), 4-acetyl pyridine (1), 3-benzoyl pyridine (1), 4-benzoyl pyridine (1), 2,2,'-dipyridylketone (2), methylbenzoylformate (1), xanthone (1), dibenzoylmethane (3), ethylbenzoyl acetate (3), fluorenone (3), benzophenone (1), 4-aminobenzophenone (3), benzophenone-2-carboxylic acid (1), benzophenone-4-carboxylic acid (1), 4-methylbenzophenone (1), 4,4'-bis-(trimethylammonium)-benzophenone dichloride (3).

D. Aromatic diketones: benzil (3), acenaphthenequinone (1), phenanthrenequinone (1)*, 1,2-naphthoquinone (1)*, 1,4-naphthoquinone (1)*, anthraquinone (1), 2-t-butyl-anthraquinone (1).

E. Miscellaneous: benzaldehyde (1), acridine (1)*, nitrobenzene (3), lumichrome (3), fluorescein (3), benzoquinone (2)*, N,N'-dimethyl-4,4'-bipyridylium dimethosulphate (3), 7-chloro-9-diethylaminoethylisoalloxazine (3) and lumiflavin (l).

What we claim is:

1. A process for the oxidation of an organic substrate comprising under homogeneous conditions the photochemical activation of an organic hydrogen abstracting agent which is in contact with an organic substrate to form a reactive species capable of abstracting a hydrogen atom from the organic substrate, and allowing said reactive species to abstract a hydrogen atom from said substrate, one of the radicals thus produced being reconverted to the organic hydrogen abstracting agent by the presence of a compound of a variable valency metal initially present in the higher of the two valency/oxidation states and reduced to the lower of the valency/oxidation states during the process, the process conditions being such that the compound of the variable valency metal is completely soluble in the reaction system.

2. An oxidation process as claimed in claim 1 wherein the variable valency metal is copper and the two valency/oxidation states are $Cu^{II}$ and $Cu^{I}$.

3. An oxidation process as claimed in claim 2 wherein the compound of copper used is copper (II) acetate monohydrate.

4. An oxidation process as claimed in claim 1 wherein the compound of the variable valency metal contains organic acid ligands.

5. An oxidation process as claimed in claim 4 wherein the organic acid ligands are selected from benzoic, acetic, pivalic, tri-fluoromethyl sulphonic, benzene sulphonic and trifluoroacetic acid ligands.

6. An oxidation process as claimed in claim 1 wherein the organic hydrogen abstracting agent is a benzophenone or anthraquinone compound.

7. An oxidation process as claimed in claim 6 wherein the anthraquinone compound is an anthraquinone substituted with at least one lower alkyl group.

8. An oxidation process as claimed in claim 1 wherein the organic hydrogen abstracting agent is selected from benzophenone, anthraquinone, 2-t-butyl anthraquinone and 4-benzoyl benzoic acid.

9. An oxidation process as claimed in claim 1 conducted in a solvent medium which will react with a carbonium ion produced in the process.

10. An oxidation process as claimed in claim 9 wherein the solvent medium comprises an organic acid medium free of abstractable hydrogen atoms.

11. A product obtained by a process as claimed in claim 10 which is an ester of an organic acid produced from a hydrocarbon substrate reacted in a said organic acid medium.

12. An oxidation process as claimed in claim 1 wherein the substrate is an organic compound represented by the formula:

$R^1R^2CH-CHR^3R^4$ wherein $R^1R^2R^3$ and $R^4$ 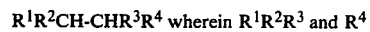

which may be the same or different are hydrogen, hydrocarbyl or substituted hydrocarbyl groups.

13. An oxidation process as claimed in claim 12 wherein the hydrocarbyl groups are either substituted with F, CN or COOH groups or they contain the functional links represented by —O—, —CO— or —COO—.

14. An oxidation process as claimed in claim 1 which also comprises the re-oxidation of the variable valency metal to the higher of the two valency/oxidation states for re-use in the process.

15. An oxidation process as claimed in claim 1 wherein the organic substrate is itself a carboxylic acid containing abstractable hydrogen atoms.

16. An oxidation process as claimed in claim 1 wherein the organic hydrogen abstracting agent is used on a solid support.

17. An oxidation process as claimed in claim 1 wherein the hydrogen abstracting agent interacts in a regio-selective manner with the substrate being oxidised in the process so that pre-selected molecular positions on the substrate are oxidised preferentially.

18. A product obtained by a process as claimed in claim 1 which is an alkene obtained from an alkane substrate or which contains an alkenyl group formed from an alkyl group in the substrate.

19. A process for the selective oxidation of a compound of formula $$(R^1Y)_n-Ar-CHR^2R^3 \quad (1)$$

to a compound of formula $$(R^1Y)_n-Ar-\underset{OCOR^4}{\overset{|}{C}}-R^2R^3 \quad (2)$$

comprising contacting the compound of formula (1) with a hydrogen abstracting agent which on photochemical activation forms a reactive species capable of abstracting a hydrogen from the compound of formula (1) and irradiating the abstracting agent with light of a wavelength capable of exciting the agent to the state in which it will abstract a hydrogen atom from the compound of formula (1), the reaction being conducted in the presence of a compound of a variable valency metal initially in the higher of two valency/oxidation states which is capable of oxidising both of the radicals produced by the hydrogen abstraction and which thereby regenerates the hydrogen abstracting agent and converts the compound of formula (1) to an intermediate which will form a compound of formula (2) by means of a reaction with an acid of formula $R^4COOH$, a process wherein Ar is an aromatic nucleus;

$R^1$, $R^2$ and $R^3$, which may be the same or different, represent hydrogen atoms, aromatic or saturated or unsaturated aliphatic; hydrocarbyl groups; Y is either a direct link or is an —O—, —CO—,

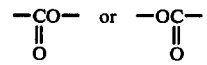

group provided that such groups $R^1Y$, $R^2$, $R^3$ do not contain readily abstractable hydrogens and any of $R^1$, $R^2$ and $R^3$ may be linked alone or in conjunction with the aromatic nucleus to form a further ring system;

n is a small integer and $R^4$ is an aliphatic or an aromatic hydrocarbyl group optionally containing substituents but which does not contain readily abstractable hydrogen atoms.

20. A process as claimed in claim 19 wherein the acid $R^4COOH$ is acetic acid, pivalic or benzoic acid.

21. The product 3-phenoxybenzyl acetate whenever produced by a process as claimed in claim 19.

* * * * *